United States Patent [19]

Talwar et al.

[11] Patent Number: 5,196,197
[45] Date of Patent: Mar. 23, 1993

[54] REVERSIBLE FERTILITY CONTROL FOR PREVENTION OF PREGNANCY IN FEMALES

[75] Inventors: Gursaran P. Talwar; Shakti Upadhyay; Charu Kaushic; Amarjeet Singh; Madan G. Sharma, all of New Delhi, India

[73] Assignee: National Institute of Immunology, New Delhi, India

[21] Appl. No.: 574,307

[22] Filed: Aug. 28, 1990

[51] Int. Cl.$^5$ .............................................. A61K 35/78
[52] U.S. Cl. ...................... 424/195.1; 424/DIG. 12; 424/DIG. 14
[58] Field of Search ............... 424/195.1, DIG. 14, 424/DIG. 12; 436/510, 814; 435/806; 128/830, 832, 833, 834

[56] References Cited

PUBLICATIONS

CA 102(7):56308y Sinha et al. (1984).
"Intravaginal Contraceptive Material", Dasqupta et al. CA 80 (2):6978v (1973).
"Spermicidal saponins from the fruits of Sapindus species commonly known as soap nut", CA 98(14) 113706b by Garg et al. (1982).
"Neem Oil as a Vaginal Contraceptive," Sinha et al. CA:100 (17) 132717g (1984).

Primary Examiner—John W. Rollins
Attorney, Agent, or Firm—Ladas & Parry

[57] ABSTRACT

There is provided a means for reversible fertility control for prevention of pregnancy in female mammals for several months through the use of neem oil or its components, applied locally to the uterus. There is also provided a spermicidal composition containing neem oil or its components in combination with reetha extract as a vaginal cream.

8 Claims, 2 Drawing Sheets

REVERSIBLE FERTILITY CONTROL FOR PREVENTION OF PREGNANCY IN FEMALES

The present invention relates to the control of fertility and the prevention of pregnancy in females. In particular, the invention relates to a new method for blocking reversibly the fertility of a female without disturbing physiological functions such as hormonal profiles and without impairment of ovulation or libido. The invention also includes within its ambit spermicidal compositions for local application in the vagina.

The control of population particularly in the developing countries of the world has become an economic necessity. Although a number of methods for population control, popularly referred to as "family planning", are currently available, there is a continuing need for newer and improved methods. In particular, it has been the objective of researchers to develop population control methods which do not require day to day application or intake, which are free from the risk of user failure or side effects, which do not impair the normal reproductive functions and, above all, are reversible.

Certain family planning methods such as vasectomy and tubal ligation are largely irreversible and even though surgery is available for recanalisation, this is an expensive procedure. Furthermore, on the evidence of even the best series of surgical operations for the re-establishment of the passage of sperm or eggs, the percentage of successful cases where fertility is actually regained is small indeed. These characteristics generally dissuade couples from opting for these methods till a fairly late stage in their reproductive life.

In so far as known population control methods are concerned, the use of spermicidal preparations in reasonably convenient and has found fairly wide acceptability. Unfortunately, the major drawback in the case of spermicides is their relatively low efficacy and high failure rate (Zatuchni et al., 1979).

Among contraceptives which on a single administration can confer protection against pregnancy for a few months there can be mentioned injectable steroid depots of medroxy-progesterone, norethindrone acetate. Such depots are capable of blocking fertility for periods of from 1 to 3 months. Unfortunately, the major disadvantage to depot steroid is amenorrhea which is not acceptable in some cultures. Moreover, these chemically synthesized steroids stop ovulation altogether.

For these reasons, safe reversible methods for preventing pregnancy for a desired period are very much in demand all over the world.

The object of the present invention is therefore the provision of a method of fertility control or family planning which is reversible and offers a couple the opportunity to reproduce once again if they so desire without permanent impairment of normal reproductive faculties.

A further object of this invention is the provision of a family planning method which does not entail a day-to-day intake or application, which is substantially free of risk of failure, which is not physically or psychologically unpleasant in its application and which has no adverse side effects.

A still further object of the invention is the provision of a more effective spermicidal composition employing natural plant extracts for short-term local application within the vagina which composition is free of irritability and side effects and which is effective in suppressing the growth of undesirable microorganisms.

The applicants' efforts towards the achievement of such objects have led them to study afresh an ancient and indigenous plant already well known for its utility in other areas, the neem tree. The neem tree (Azadirachta indica or Melia azadirachta) found throughout India is used in indigenous and household medicine for different puposes. Almost every part of the tree has been utilized for treatment of various disorders and diseases such as arthritis (Pillai and Santhakumari, 1981, a, b), inflammation (Okpanyi and Ezeukwu 1981), malaria (Obbaseki and Jegede-Fadunsin, 1986). Neem oil in particular, also known as oil of margosa, has been shown to possess anti-diabetic (Chakrabarty and Poddar, 1984; Sharma et al., 1983), anti-bacterial (Singh and Sastry 1981) and anti-fungal (Kher and Chaurasia, 1977) properties.

Although earlier experimental studies have also shown the anti-fertility effect of neem oil, the degree of efficacy, a weak point in barrier methods, is improved by the composition of the present invention where an extract of an additional plant has been included. Neem oil alone has also experienced acceptability problems in women as a result of the unpleasant odor of the oil. Fortunately, these problems are taken care of by the inventive formulation.

Neem oil has also been used as an abortifacient. The effect was, however, less evident following oral administration than vaginal application in pregnant rats. In one of the studies, reported by Riar et al. (1988), neem oil (0.075 ml) was applied intra-vaginally on days 2,3,4 or 4,5,6 or 7,8,9 of pregnancy in rats. Pregnancy was terminated. On the other hand, according to Lal et al. (1986), neem oil (0.10 ml) administered to pregnant rats daily from day 1 to day 10 of pregnancy either by oral or intra-vaginal routes resulted in the termination of pregnancy in only 40 per cent of cases.

In contradistinction to what was hitherto believed to be the characteristics of neem oil, the method of the present invention has been developed on the basis of findings which are both novel and surprisingly different from what was previously described. According to the invention, a small amount of a highly purified, cold extracted neem oil is applied into the uterus with the help of a catheter. In respect of monkeys, the dosage is from 0.2 to 2.0 ml, preferably 1 ml. In the case of rodents, an amount of from 0.05 to 0.2 ml is applied to each uterine horn. Following such treatment, animals of established fertility become infertile although ovulation takes place normally and the animals mate in the normal way. No ill effect of any type has been noted in the subjects following the treatment. Fertility in the animals is restored after a period of from 4 to 6 months.

Accordingly, the present invention provides a method for blocking reversibly the fertility of a female without impairing ovulation which comprises applying a predetermined amount of neem oil to the uterus of the female subject.

Based on the findings in respect of monkeys and rodents, the suggested dosage for female human subjects can range up to 4 ml.

A single administration of neem oil has been found sufficient to render the subject infertile for several months with a fertility block produced in 100% of the cases tested.

According to a further feature, the present invention also provides a spermicidal composition comprising a dispersion of neem oil in a pharmaceutically acceptable carrier or base therefor.

In accordance with a preferred embodiment, the spermicidal composition comprises a dispersion or emulsion of neem oil and the water-soluble extract of the fruit of Sapindus mukerossi (known popularly in India as "reetha") in a cream base. Such cream can be prepared employing conventional pharmocopial grade emulsifiers.

According to a specific embodiment, the spermicidal composition of the invention comprises from 5% to 25% by weight neem oil and from 0.5% to 2% by weight reetha extract, the balance being made up of the emulsifier and cream base.

The invention will now be described in greater detail in the following examples.

EXAMPLE 1

Female rats of proven fertility were given 1/10th of a milliliter (0.1 ml) of neem oil in one or both uterine horns. The animals were kept for mating with males also of proven fertility. Those females which had received neem oil in both uterine horns did not become pregnant for periods ranging from 3½ to 6 months. However, they mated normally with males and sperm positivity in vaginal smears was observed in each rat on 4 to 12 occasions. In contradistinction, all female rats receiving peanut oil in a similar manner in their uterine horns became pregnant.

This parallel control experiment excludes the non-specific effect of either an oil or the process of delivery of it in the uterus. The typical results on ten rats are summarized in Table 1 which follows hereafter.

TABLE 1

INTRA-UTERINE APPLICATION OF NEEM OIL
ANIMAL MODEL: FEMALE WISTAR RATS OF
PROVEN FERTILITY (AVERAGE LITTER SIZE: 10)
FERTILITY RECORD: OBSERVATION PERIOD
6 MONTHS

| ANIMAL NUMBER | NUMBER OF SPERM POSITIVE MATINGS | PERIOD OF INFERTILITY* (DAYS) | LITTER SIZE AFTER REGAIN OF FERTILITY |
|---|---|---|---|
| EXPERIMENTAL GROUP: NEEM OIL (100 ul/horn) | | | |
| 1 | 6 | 180 | — |
| 2 | 8 | 141 | 3 (10)# |
| 3 | 5 | 137 | — |
| 4 | 5 | 107 | 2 |
| 5 | 12 | 180 | — |
| 6 | 5 | 122 | 2 (9)# |
| 7 | 4 | 133 | 2 |
| 8 | 4 | 112 | 9 |
| 9 | 7 | 180 | — |
| 10 | 5 | 180 | — |
| CONTROL GROUP: PEANUT OIL (10 ul/horn) | | | |
| 1 | 2 | 14 | 10 |
| 2 | 1 | — | 9 |
| 3 | 1 | — | 10 |
| 4 | 1 | — | 12 |
| 5 | 1 | — | 9 |
| 6 | 2 | 6 | 9 |
| 7 | 1 | — | 8 |
| 8 | 1 | — | 10 |
| 9 | 1 | — | 12 |
| 10 | 1 | — | 9 |

*Number of days from the time animals were put on continuous mating to the date of last sperm positive mating leading to pregnancy
Number of litters in the second pregnancy What is surprising is that normalcy of ovulation in animals not becoming pregnant is maintained. No side effects of any discernible type are noticed. This normalcy of ovulation in animals not becoming pregnant is best demonstrated by an experiment carried out on rats. Female rats have two uterine horns. Neem oil was injected into one of the horns and peanut oil into the other horn. On mating, these animals showed embryos present in the horn receiving peanut oil, whereas no evidence of embryos was noticeable in the horn receiving the neem oil. Proof of this can be discerned from the photographs presented as FIGS. 1 and 2 accompanying this specification.

Figure 1:
FIG. 1 is a photograph illustrating the exposed viscera, including the uterine horns, of a female rat on the sixteenth day of pregnancy.
Figure 2:
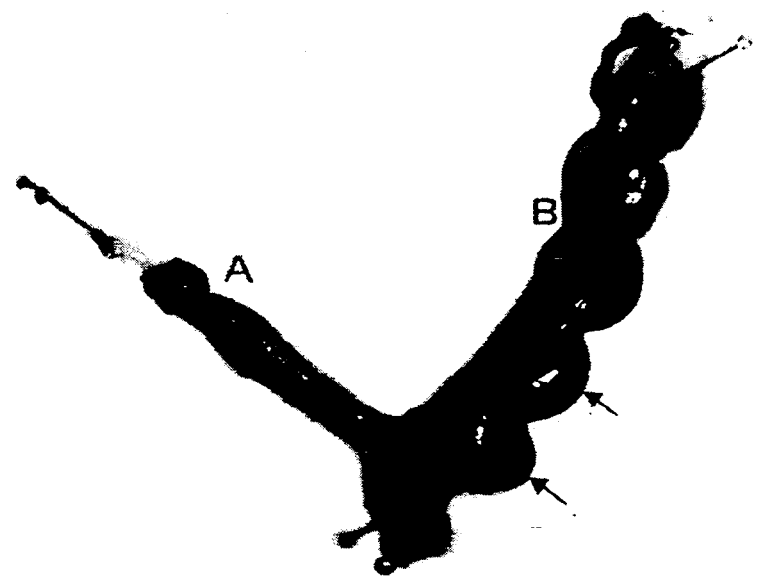
FIG. 2 is a photograph showing only the dissected horns of the same rat. The right uterine horn marked A to which neem oil was administered shows no implantations whereas the left uterine horn marked B to which peanut oil was adminstered shows five implantation sites.
Figure 3:

However, FIG. 3, which is a photomicrograph of a portion of the right ovary of the animal shown in FIG. 1, shows the presence of corpus luteum (CL) indicating that intra-uterine administration of neem oil does not inhibit ovulation.

The mechanism by which this remarkable effect of the neem oil is exercised is suggested by the detailed histological studies carried out by the applicants. Neem oil is taken up by the uterine macrophages which increase considerably in number within the uterine epithelium. Thereafter, following each natural mating, the macrophages and lymocytes congregate in large numbers in the uterine lumen as and when the blastocyst reaches the uterus. The presence of these immunoreactive cells prevents the nidation of the embryo and causes its demise. They do not exercise any apparently toxic effect on other cells of the uterus as is evident from histological studies.

The ability of these leukocytic cells to interfere in pregnancy is a new and recent concept. They may either have a direct effect on the blastocyst or their effect may be mediated by soluble factors, the monokines and lymphokines, produced by them. Cell mediated immunity is also seen to prevail in natural infertility cases (Anderson and Hill 1988; Hill et al., 1987). In the present approach, it is deliberately induced in a reversible manner using a traditional plant product, viz. neem oil, in females.

What is more, these effects are not unique to rats as a species. Rabbits also showed blocks in fertility following a single intra-uterine exposure to neem oil administered non-surgically by a catheter through the vagina. None of the three animals so treated became pregnant for more than 3 months of observation period even after 10 matings at intervals of 10 days. Control rabbits under similar circumstances became pregnant following the first mating and the results of the experiment are summarized in Table 2 which is set out hereunder.

TABLE 2

INTRA-UTERINE APPLICATION OF NEEM OIL
ANIMAL MODEL: FEMALE RABBIT
FERTILITY RECORD:

| ANIMAL NUMBER | NUMBER OF SPERM POSITIVE MATINGS | PERIOD OF INFERTILITY* (DAYS) | LITTER SIZE AFTER REGAIN OF FERTILITY |
|---|---|---|---|
| EXPERIMENTAL GROUP: Neem Oil (1 ml) | | | |
| 1 | 10 | 95 | 4 |

TABLE 2-continued

INTRA-UTERINE APPLICATION OF NEEM OIL
ANIMAL MODEL: FEMALE RABBIT
FERTILITY RECORD:

| ANIMAL NUMBER | NUMBER OF SPERM POSITIVE MATINGS | PERIOD OF INFERTILITY* (DAYS) | LITTER SIZE AFTER REGAIN OF FERTILITY |
|---|---|---|---|
| 2 | 10 | 180 | 4 |
| 3 | 10 | 116 | 6 |
| CONTROL GROUP: Peanut oil (1 ml) | | | |
| 4 | 1 | 0 | 4 |
| 5 | 1 | 0 | 3 |
| 6 | 2 | 10 | 4 |

*Number of days from the time of administration of neem oil to the date of last mating leading to pregnancy.

Similarly, six female bonnet monkeys of proven fertility remained infertile for more than five cycles following a single non-surgical intra-uterine administration of neem oil in spite of being mated with male monkeys of proven fertility. On the other hand, control monkeys became pregnant within the first or second cycle. These results are summarized in Table 3 which follows hereafter.

TABLE 3

INTRA-UTERINE APPLICATION OF NEEM OIL
ANIMAL MODEL: FEMALE BONNET MONKEY
FERTILITY RECORD:

| ANIMAL NUMBER | NUMBER OF MATED CYCLES | PREGNANCY STATUS |
|---|---|---|
| EXPERIMENTAL GROUP: Neem Oil (1 ml) | | |
| 1 | 6 cycles | Not pregnant |
| 2 | 6 cycles | Not pregnant |
| 3 | 6 cycles | Not pregnant |
| 4 | 6 cycles | Not pregnant |
| 5 | 6 cycles | Not pregnant |
| 6 | 6 cycles | Pregnant after 5 cycles |
| CONTROL GROUP: Peanut Oil (1 ml) | | |
| 7 | 1 cycle | pregnant |
| 8 | 1 cycle | pregnant |
| 9 | 2 cycles | Pregnant after 2 cycles |

The employment of neem oil as a spermicide and its effect is described hereafter in the following examples.

EXAMPLE 2

Fourteen female monkeys with proven fertility records were selected from among those in a colony. 1 ml of neem oil was administered to the vaginas of nine female monkeys by means of an applicator before mating of the monkey with a male of proven fertility. A separate control group of five monkeys received 1 ml of peanut oil. Of the nine monkeys to which neem oil was applied intravaginally, only one became pregnant over 50 cycles of observation period whereas all five monkeys of the control group became pregnant within one or two cycles of mating. The results of this study are set out in Table 4 hereafter.

TABLE 4

INTRA-VAGINAL APPLICATION OF NEEM OIL
ANIMAL MODEL: FEMALE BONNET MONKEY
FERTILITY RECORD:

| NUMBER OF ANIMALS | NUMBER OF MATED CYCLES | SPERM POSITIVE VAGINAL SMEARS | CONCEPTION/TOTAL NUMBER OF CYCLES OF OBSERVATION |
|---|---|---|---|
| EXPERIMENTAL GROUP: NEEM OIL (1 ml) | | | |
| 9 | 4 to 6 | 450 | 1/50 |
| CONTROL GROUP: Untreated | | | |
| 5 | 1 to 2 | 15 | 5/7 |

EXAMPLE 3

A cream was prepared by emulsifying 25% by weight of neem oil and 1% by weight of water soluble reetha extract in a conventional cream base. 1 ml of the cream thus prepared was applied intravaginally to female monkeys of proven fertility who were then allowed to mate repeatedly with male monkeys also of proven fertility. The cream did not interfere with the copulation nor did it affect the libido of the animals. It did not disturb ovulation of the female monkey. Laprascopic examination of the vaginas of the monkeys after 20 daily application did not reveal any inflamatory response. The results of this experiment are set out in Table 5 hereafter.

TABLE 5

INTRA-VAGINAL APPLICATION OF NEEM OIL CREAM
ANIMAL MODEL: FEMALE BONNET MONKEY
FERTILITY RECORD:

| NUMBER OF ANIMALS | NUMBER OF MATED CYCLES | SPERM POSITIVE VAGINAL SMEARS | CONCEPTION/TOTAL NUMBER OF CYCLES OF OBSERVATION |
|---|---|---|---|
| EXPERIMENTAL GROUP: Neem Oil Cream (1 ml) | | | |
| 8 | 3 to 7 | 400 | 1/44 |
| CONTROL GROUP: Untreated | | | |
| 2 | 1 to 2 | 15 | 2/4 |

The animals treated according to Examples 1, 2 and 3 remained entirely healthy. Their food intake and weight gain was normal and no noticeable ill effects were evident.

Because of the inherent medicinal properties of neem, the method of the present invention and the spermicidal cream afford the added advantage of vaginal and uterine protection against veneral infections caused by microorganisms, viruses and fungi. Thus, recourse to the present method brings about the added advantage of vaginal hygiene by suppressing and killing undesirable pathogenic microorganisms.

It is interesting to note that no day to day application of the effective agent, neem oil, is required, as is the case when condoms and pills are employed for contraception. Once given, the infertility is induced for periods ranging from 3 to 6 months. This fact offers a considerable advantage as it makes the recipient free from user failure risk. The method has been found to be successful in every case pointing to its high efficacy.

Most importantly, the method of the present invention offers a reversible modality in fertility control. Subjects rendered infertile by instillation of neem oil could become pregnant after a period ranging from 3 to 6 months of blocked fertility.

We claim:
1. An antifertility agent comprising neem oil and a reetha extract wherein the neem oil is present in a con- centration of about 10%–25% weight/weight and the concentration of the reetha extract is about 0.5–1% weight/weight.

2. An antifertility agent comprising neem oil and a reetha extract wherein the neem oil is present in a concentration of about 25% weight/weight and the concentration of reetha extract is about 0.5–1% weight/weight.

3. An antifertility agent as claimed in claim 2 further comprising an emulsifier and a cream base.

4. A method for reversibly blocking the fertility of a female mammal without impairing ovulation in said mammal, which comprises introducing prior to an act of sexual intercourse an antifertility agent according to claim 2 directly into the uterus of the female in an amount sufficient for the reversible blocking of the fertility of said mammal wherein further introduction of the antifertility agent into the uterus occurs not less frequently then after two acts of sexual intercourse.

5. A method according to claim 4 wherein the amount of antifertility agent introduced into the uterus is sufficient to block the fertility of said mammal for about three to six months.

6. A method as claimed in claim 4 wherein said antifertility agent is applied to the uterus in a dosage not exceeding 4 ml.

7. A method as claimed in claim 4 wherein the antifertility agent is introduced directly into the uterus of said mammal through a catheter.

8. An antifertility agent according to claim 2 wherein the neem oil is purified neem oil.

* * * * *